United States Patent [19]
Colpan et al.

[11] Patent Number: 5,792,651
[45] Date of Patent: Aug. 11, 1998

[54] ENHANCEMENT OF THE TRANSFECTION EFFICIENCY OF NUCLEIC ACIDS BY USING ISOPROPANOL IN AQUEOUS SOLUTIONS

[75] Inventors: Metin Colpan, Essen; Joachim Schorr, Düsseldorf, both of Germany

[73] Assignee: Qiagen GmbH, Hilden, Germany

[21] Appl. No.: 687,530

[22] PCT Filed: Feb. 3, 1995

[86] PCT No.: PCT/EP95/00390

§ 371 Date: Oct. 11, 1996

§ 102(e) Date: Oct. 11, 1996

[87] PCT Pub. No.: WO95/21178

PCT Pub. Date: Aug. 10, 1995

[30] Foreign Application Priority Data

Feb. 7, 1994 [DE] Germany .................. 44 03 693.0
Feb. 7, 1994 [DE] Germany .................. 44 03 692.2
Sep. 1, 1994 [DE] Germany .................. 44 31 125.7
Sep. 14, 1994 [DE] Germany .................. 44 32 654.8

[51] Int. Cl.$^6$ .................. C12N 1/06; C12N 15/10
[52] U.S. Cl. .................. 435/270; 536/25.41
[58] Field of Search .................. 435/220; 536/25.41

[56] References Cited

FOREIGN PATENT DOCUMENTS

| | | |
|---|---|---|
| 0512767A1 | 5/1991 | European Pat. Off. . |
| 0512768A1 | 5/1991 | European Pat. Off. . |
| 4321904A1 | 7/1993 | Germany . |
| 93-11221 | 6/1993 | WIPO . |

*Primary Examiner*—James Ketter
*Attorney, Agent, or Firm*—Jacobson, Price, Holman & Stern, PLLC

[57] ABSTRACT

Use of isopropanol in aqueous solutions for chromatographic isolation of nucleic acids for enhancing the transfection efficiency of the isolated nucleic acids in prokaryotic and eukaryotic cells.

11 Claims, No Drawings

ENHANCEMENT OF THE TRANSFECTION EFFICIENCY OF NUCLEIC ACIDS BY USING ISOPROPANOL IN AQUEOUS SOLUTIONS

The present invention pertains to the use of isopropanol in aqueous solutions for enhancing the transfection efficiency of nucleic acids in prokaryotic and eukaryotic cells.

Applicant's DE 36 39 949 A1 pertains to a process for the isolation and purification of nucleic acids, in particular long-chain nucleic acids. This involves the use of aqueous solutions (buffers) of relatively low ionic strength to wash the nucleic acid which is first adsorbed at low ionic strength on an anion exchange matrix. Thereafter, the nucleic acids are desorbed from the matrix using buffers with higher ionic strengths. Ethanol, inter alia, may be employed for the precipitation of nucleic acids, especially DNA. Solutions containing lower alcohols are proposed in Applicant's P 43 21 904. The solutions containing lower aliphatic alcohols are used together with high concentrations of chaotropic ions to adsorb nucleic acids on inorganic materials which have not been modified by anion exchanging groups.

Then, the nucleic acid thus isolated is frequently introduced in eukaryotic or prokaryotic cells by chemical or physical methods. This process, called transfection, is used in order to study the regulatory effect of certain genes or their expression products on the genome of the host cell. Such methods involve rather high expenditures of both work and time since a period of 10 to 14 days must be scheduled, as a rule, for performing and evaluating a single experiment. Therefore, a high interest exists in seeing, for example, that the plasmid DNA to be studied is introduced in as many cells of a cell culture as possible. The frequency of intake of foreign DNA offered, which is called transfection efficiency, depends on a variety of factors. Usually, the transfection efficiency depends, in addition to the quality of the cell culture and the transfection method, substantially on the quality or purity of the plasmid DNA used.

In Ehlert et al., Biotechniques 14, 1993, 546, it could be shown that plasmid DNA prepared using the QIAGEN® anion exchange material according to the method described in DE 36 39 949 will give a transfection efficiency which is improved by 70% over that of DNA purified by cesium chloride density gradient centrifugation.

Surprisingly, the transfection rate known from Biotechniques 14, 1993, 546, could be enhanced by up to 20% by using isopropanol in aqueous solutions which are employed for the isolation of nucleic acids.

Thus, the present invention pertains to a process for the isolation of nucleic acids which has an improved transfection rate over that known from DE 36 39 949 A1 by using aqueous solutions containing isopropanol for the separation and isolation of nucleic acids on anion exchangers.

In a preferred embodiment, the isopropanol will be present in the aqueous solutions in an amount of from 1 to 50% by volume, in particular from 5 to 25% by volume, particularly preferred from 10 to 15% by volume. The aqueous solutions may also include, in particular, salts of monovalent or divalent cations commonly used for anion exchange chromatography, such as sodium chloride, potassium chloride etc., or combinations thereof. Preferably, the aqueous solutions are buffered with buffer materials conventionally used in molecular biology, such as TRIS/HCl, MOPS etc. and have pH values of between 6 and 9.

The use of isopropanol according to the invention can be applied, in particular, in the isolation of DNA, such as plasmid DNA, but is not restricted to such types of DNA.

The nucleic acids obtained using isopropanol according to the invention are particularly suitable for being employed in gene-therapy methods.

According to the invention, solutions are also claimed which may contain isopropanol in amounts of from 5 to 60% by volume. These are, in particular, the washing buffers which can be used according to DE 36 39 949 A1. Those buffers contain 0.5 to 1.5M sodium chloride or potassium chloride and 20 to 80 mM MOPS or TRIS/HCl at a pH value of 6 to 8. According to the invention, aqueous solutions are also claimed including from 5 to 60% by volume of isopropanol which additionally contain 1.0 to 2.0M sodium chloride or potassium chloride and 20 to 80 mM TRIS/HCl at a pH value of 8 to 9.

DE 39 13 814 A1 describes in general terms aqueous systems in buffers which may be used for the electroelution of gels. The buffer systems described therein include, for instance, sodium chloride, buffer salts, such as MOPS, and lower alcohols, especially $C_1$ to $C_4$ alcohols. However, the salt concentration of these buffers is rather high since 1.5M of sodium chloride or above is explicitly required.

An aqueous system containing isopropanol can preferably be used in the process for the depletion or removal of endotoxins as proposed in the German Patent Application P 44 31 125.7. This patent application proposes a process in which endotoxins from preparations containing active ingredients designated for therapeutical use are depleted or removed. Those preparations are preferably obtained from natural sources by genetic engineering and/or biotechnology. The depletion or removal of the endotoxins is performed by treating the samples with chromatographic material wherein the natural sources are lysed, the fractions obtained are optionally centrifuged, filtered or treated with affinity chromatographic material. The fractions obtained are preincubated with an aqueous salt solution and detergents, treated with anion exchange material and subsequently washed with another salt solution. The active ingredients are eluted from the anion exchanger and then are further purified in a per se known manner. If a nucleic acid is isolated, for instance, which can be used in gene-therapy methods and has been subjected to a removal or depletion of endotoxins according to P 44 31 125.7, an enhancement of transfection efficiency of up to 50% can be observed as compared to preparations in which ethanol has been used in the preparation solutions.

The invention will be illustrated in more detail by the following examples.

EXAMPLE 1

In the following, plasmid DNA from *E. coli* as the nucleic acid was separated and isolated in analogy to the process mentioned in DE 36 39 949 A1. This involves adsorption of the nucleic acid on the anion exchange material described in DE 36 39 949 A1 (QIAGEN®, Diagen GmbH, Germany). Washing was performed with a buffer of the composition: 1.0M NaCl, 50 mM MOPS, 15% isopropanol, pH 7.0.

Thereafter, the plasmid DNA was eluted with the isopropanol containing buffer of the composition: 1.25M NaCl, 50 mM TRIS/HCl, 15% by volume isopropanol, pH 8.5.

It could be seen that the yield of plasmid DNA from *E. coli* could be enhanced by about 10% as compared to the known preparations using ethanol.

Then, transfection experiments were performed with the DNA thus obtained. The transfection efficiency was determined by measuring the lacZ activity using NIH 3T3 cells. These cells were transfected by the calcium phosphate method (Graham, F. L., and A. J. van der Eb (1973) "A New Technique for the Assay of Infectivity Human Adenovirus 5 DNA", Virology 52: 456–467) with 1 µg of the reporter construction pRSVlacZ (Lucibello, F. C., and R. Müller (1989) "Sensitive Microscale Assay for the Analysis of motor Activity in Eukaryotic Cells", Methods Mol. Biol. 1: 9–18).

Table shows the transfection efficiency using a number of alcohols, i.e. ethanol (superpure and denatured), isopropanol and n-butanol.

| | % lacZ activity | | | |
|---|---|---|---|---|
| Experiment No. | 15% ethanol superpure in buffer QBT, QC, QF | 15% ethanol denatured in buffer QBT, QC, QF | 15% isopropanol in buffer QBT, QC, QF | 15% n-butanol in buffer QBT, QC, QF |
| 1 | 80 | 78 | 95 | 20 |
| 2 | 75 | 70 | 92 | 12 |
| 3 | 70 | 70 | 98 | 9 |
| 4 | 85 | 80 | 100 | 15 |
| 5 | 83 | 78 | 97 | 18 |

From the values listed in the table, there can be clearly seen the high transfection efficiency of DNA obtained with buffers containing isopropanol.

EXAMPLE 2

Plasmid DNA was isolated according to example 1. Prior to charging onto the anion exchange column, however, the lysate was passed over a loose packing of diatomaceous earth as described the German Patent Application P 44 32 654.8. Then, an endotoxin depletion was performed according to the method described in P 44 31 125.7. An aqueous solution was employed including 750 mM sodium chloride, 10% Triton X-100/50 mM MOPS at a pH of 7.0. The DNA thus prepared was transfected into LMH liver cells by means of cationic liposomes (DOTAP, Boehringer Mannheim). An enhancement of transfection efficiency of 50% is seen as compared to a DNA preparation according to the prior art document DE 36 39 664.9 A1.

We claim:

1. In a method of chromatographic isolation of nucleic acids, whereby nucleic acids are eluted using an aqueous solution, the improvement comprising eluting the nucleic acids using isopropanol in aqueous solution, which effects isolated nucleic acids having enhanced transfection efficiency in procaryotic or eucaryotic cells.

2. The method of claim 1 wherein said isopropanol is present in said aqueous solutions in an amount of from 1 to 50% by volume.

3. The method of claim 1 wherein said isopropanol is present in said aqueous solutions in an amount of from 5 to 25% by volume.

4. The method of claim 1 wherein said isopropanol is present in said aqueous solutions in an amount of from 10 to 15% by volume.

5. The method of claim 1 wherein said aqueous solution contains salts of monovalent or divalent cations.

6. The method of claim 5, wherein said aqueous solution contains sodium chloride, calcium chloride, potassium chloride, or combination thereof.

7. The method of claim 1 wherein said aqueous solution is a buffered solution.

8. The method of claim 1 wherein said nucleic acid DNA is plasmid DNA.

9. The method of claim 1 for the preparation of nucleic acids for gene therapy.

10. An aqueous solution containing 0.5 to 1.5M sodium chloride or potassium chloride, 10 to 100 mM MOPS or TRIS/HCl, and from 5 to 60% by volume of isopropanol at a pH value of 6 to 8.

11. An aqueous solution containing 1.0 to 2.0M sodium chloride or potassium chloride, 10 to 100 mM TRIS/HCl, and from 5 to 60% by volume of isopropanol at a pH value of 8 to 9.

* * * * *